United States Patent
Wolf et al.

(10) Patent No.: US 12,171,545 B2
(45) Date of Patent: Dec. 24, 2024

(54) ROBOTIC SHOE FOR DIAGNOSIS AND REHABILITATION OF GAIT ANOMALIES

(71) Applicant: TECHNION RESEARCH AND DEVELOPMENT FOUNDATION LIMITED, Haifa (IL)

(72) Inventors: Alon Wolf, Haifa (IL); Hadar Shaulian, Haifa (IL)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 16/889,173

(22) Filed: Jun. 1, 2020

(65) Prior Publication Data

US 2020/0390368 A1 Dec. 17, 2020

Related U.S. Application Data (63) Continuation of application No. PCT/IL2018/051069, filed on Sep. 23, 2018.
(Continued)

(51) Int. Cl.
*A61B 5/11* (2006.01)
*A43B 17/00* (2006.01)
*A61B 5/00* (2006.01)

(52) U.S. Cl.
CPC ............ *A61B 5/112* (2013.01); *A43B 17/003* (2013.01); *A61B 5/1108* (2013.01);
(Continued)

(58) Field of Classification Search
CPC .................................................. A61B 5/6807
See application file for complete search history.

(56) References Cited

U.S. PATENT DOCUMENTS 6,979,287 B2  12/2005  Elbaz et al.
8,458,930 B2 *  6/2013  Ha .......................... A43B 7/144
                                                    36/97
(Continued)

FOREIGN PATENT DOCUMENTS

CN      104102236 A   * 10/2014
IN      201641011051    3/2016
WO      2018110621 A1   6/2018

OTHER PUBLICATIONS

Blanc et al.,"Flexible Medical Devices: Review of Controllable Stiffness Solutions", Actuators, pp. 1-31 (Jul. 2017).
(Continued)

*Primary Examiner* — Benjamin S Melhus
*Assistant Examiner* — Severo Antonio P Lopez
(74) *Attorney, Agent, or Firm* — FISHERBROYLES, LLP; Roger L. Browdy; James E. Mrose (57) ABSTRACT

A robotic shoe which provides real-time feedback regarding forces acting on the foot of the user, in order to modify these forces in a corrective or diagnostic manner. The shoe comprises an insole equipped with embedded pressure sensors enabling it to continuously monitor the ground reaction forces (GRF) and the foot center of pressure (COP) while the user is standing, walking, and running. The insole COP and GRF readings are input to a programmable system that shifts the COP trajectory dynamically in a patient-specific manner via the robotic platform of the shoe. The robotic platform contains motors that control elements whose movement manipulates the forces acting on the foot and lower limb, resulting in modification of the GRF. Closed loop feedback enables a dynamic fit of an optimal COP. The COP and GRF information can be stored for analysis and diagnosis of gait and instability events accruing during locomotion.

15 Claims, 7 Drawing Sheets

Related U.S. Application Data (60) Provisional application No. 62/562,454, filed on Sep. 24, 2017.

(52) U.S. Cl.
CPC .......... *A61B 5/1126* (2013.01); *A61B 5/6807* (2013.01); *A61B 2562/0219* (2013.01); *A61B 2562/0247* (2013.01)

(56) References Cited

U.S. PATENT DOCUMENTS

| | | | | |
|---|---|---|---|---|
| 2007/0000154 A1* | 1/2007 | DiBenedetto | ........ | A61B 5/1038 36/132 |
| 2008/0134541 A1* | 6/2008 | Bar-Haim | ............ | A61B 5/1038 36/27 |
| 2015/0119767 A1* | 4/2015 | Mor | ........................ | A43B 7/147 601/28 |
| 2015/0351493 A1* | 12/2015 | Ashcroft | .............. | A61B 5/1038 36/132 |
| 2016/0235160 A1 | 8/2016 | Yee | | |
| 2016/0338644 A1* | 11/2016 | Connor | .................... | A61B 5/11 |
| 2016/0375346 A1* | 12/2016 | Czaja | ..................... | G06F 3/016 434/253 |
| 2018/0017743 A1 | 1/2018 | Morioka et al. | | |
| 2018/0104542 A1 | 4/2018 | Kwon et al. | | |
| 2018/0177436 A1 | 6/2018 | Chang et al. | | |

OTHER PUBLICATIONS

McEvoy et al., "Robotic Materials With Controllable Stiffness", The 19th International Conference on Composite Materials, pp. 1-11 (2013).

Shan et al., "Soft-matter composites with electrically tunable elastic rigidity", Smart Materials and Structures, pp. 1-9 (Jun. 2013).

* cited by examiner

| REQUIREMENT | Value | UNITS |
|---|---|---|
| Shoe size | 32 | European |
| Maximal front system size | 109 X 85 | [mm X mm] |
| Maximal rear system size | 60 X 140 | [mm X mm] |
| Mechanical system maximal height | 20 | mm |
| Mechanical system weight | 700 | g |
| Maximal carry load (vertical) | 1000 | N |
| Maximal carry load (antero-posterior) | 200 | N |
| Maximal carry load (medio-lateral) | 100 | N |
| Maximal applied moment | 9.4 | Nm |
| Range of motion along the linear axis | 45 | mm |
| Range of motion along the rotation axis | 360 | degrees |
| Control system resolution | 1 | degree |

ROBOTIC SHOE FOR DIAGNOSIS AND REHABILITATION OF GAIT ANOMALIES

FIELD OF THE INVENTION

The present invention relates to the field of diagnostic and therapeutic pressure-sensing foot-ware for ambulation, especially for providing real-time feedback to improve the user's gait.

BACKGROUND

The use of biomechanical shoes whose purpose and structure are designed to compensate for problems in a subject's gait and balance for rehabilitation and clinical treatment is a common, well-established approach. Such systems generally analyze the subject's gait for disorders, and then prescribe shoe characteristics, such that shoes constructed with those characteristics, compensate for the gait disorders. However, this approach has several drawbacks and limitations as it requires a long learning cycle to determine the optimal shoe adjustment for specific patient needs. Adjustment of the biomechanical device usually requires many cycles of trial and error to achieve an optimal patient-specific solution. Iterative adjustment is a time-consuming process that precludes achieving dynamic manipulation. A repetitious adjustment process misses the flexibility to support the subject's specific needs in various circumstances, such as the requirement for a different shoe correction for different stepping surfaces and for fatigue of the subject.

In U.S. Pat. No. 6,979,287 to A. Eibaz et al, for "Proprioceptive and Kinesthetic Footwear", there is described a shoe having two static bulbous protuberances on its underside, whose positions have been predetermined by iterative adjustments during the fitting session, intended to provide the best subjective mechanical and functional stability of the neuromuscular system, to improve or rehabilitate anticipatory (feed-forward) and reflexive (feed-back) neuromuscular control mechanism, and to regain and improve balance and postural equilibrium. However, the rehabilitative effect is fixed by this preliminary setting, which should be readjusted at regular intervals during visits to the clinic, to continue to provide the optimum therapeutic effect as the subject's neuromuscular control improves.

It is known that there is a close relationship between the position of the center of pressure on the foot, and the muscular action of the lower limbs and the lower spine, their range of motion, and the effective load applied to them. Consequently, other prior art devices have been described containing sensors measuring plantar pressure for various applications. Yet others use controllers and feedback systems to relay foot pressure information to the clinical therapist for assessment, or even to the subject, to provide warning or gait correction information. Some of these disclosures are summarized as follows.

PCT/JP2017/044821 to Yamashita entitled "Sole Measurement Device" describes a device to measure the force acting on specific parts of the sole of the foot during walking or other motion. Pressure sensors in the sole of the device transmit the pressure signal from the sensor via the input side interface, either wirelessly or via a wired connection, to a motion analyzer connected to a monitor. The data are used to propose corrective exercises or therapies for any abnormal weight distribution measured.

In Indian Provisional application IN 2016/41011051 to International Institute for Information Technology, for "Wearable integrated System to Aid Parkinson Disease Patients In Overcoming Freezing Of Gait Position", the disclosure describes a wearable, in-sole pressure detection system for detecting and relaying information regarding freezing of gait, via microcontrollers to a vibratory actuator or other feedback element on the wearer's body. The purpose of this device is to notify Parkinson disease patients during locomotion of a frozen posture, which triggers an alert, advising the patient to resume a normal walking gait. In that disclosure, the effort to respond to the signals is the patient's conscious decision rather than being inherent in the monitoring device.

US 2018/0177436 to Chang, for "System and Method for Remote Monitoring for Elderly Fall Prediction, Detection, and Prevention" contains a step segmentation processing module that measures gait dynamics via a biomechanical sensing device, a feedback interface, and the provision of real-time feedback to the patient in the form of audio, haptic or other communication to advise him/her of an increased risk of falling. Again, the effort to respond to the signals is the patient's conscious decision rather than being inherent in the monitoring device.

International PCT Application published as WO/2016/125979 to Curexo Inc. for "Gait Rehabilitation Control System and Method Therefor" describes a gait rehabilitation control system for gait training of a patient. The system contains a stationary platform having a moving tread, upon which the subject walks. The control unit comprises a gait pattern analysis unit for measuring the ground reaction force (GRF) between the patient's feet and the gait device. The device analyzes the gait pattern of the patient relative to the reaction force data and provides real time feedback by modulating the gait speed of the platform tread.

All of the prior art examples either measure forces or determine abnormalities of gait; those which provide feedback require the user or the therapist to actively act upon the information provided. Therefore, these systems are of limited use in treating gait abnormalities.

There therefore exists a need for a real-time ambulation feedback system which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems for providing real-time robotic feedback to the shoe of a user to modify the shape of the sole, such that the forces acting on the user's foot are changed in real time in accordance with the user's balancing, standing, or gait patterns. The robotic feedback can be obtained from any real time measured parameters which characterize the user's standing position or movement, whether by measuring the spatial distribution of the forces acting on the foot during such standing and ambulation, or by electromyography (EMG) measurements of the activation of the muscles of the lower limbs and even the lower spine during motion, or by the use of inertial measurements to define gait characteristics, as performed typically on the pelvis region by use of an Inertial Measurement Unit (IMU) which can be conveniently attached to the user's belt, or by a combination of any of these characteristic measurement.

The shoe used for such balance or gait compensation is a robotic biomechanical shoe, whose sole changes its spatial characteristics in real time to compensate the user's gait disorder. For those implementations using measured force sensors, the shoe comprises a special insole that is equipped with embedded pressure sensors enabling it to continuously monitor the ground reaction forces (GRF) and the foot center of pressure (COP) while the user is standing, or walking or running. The COP and GRF information can be analyzed by a control system to determine according to predetermined criteria, regarding the changes necessary in the user's gait characteristics to assist in treating gait or balance disorders, and these changes are translated by the control system into changes required in the shape of the sole of the shoe, such that the user's GRF is dynamically manipulated to assist in reducing the user's gait disorder. The system thus generates a shift of the GRF as a function of the pressure measurements performed in the insole. The changes in the sole shape affect and manipulate the forces acting on the user's foot and the lower limbs, and are executed using a real time feedback loop, which is operative to bring the spatial spread of the pressure readings by the insole to the optimum values desired for treating the user's problems in the use of his/her foot and lower limbs, or even pelvic/lower spinal region.

For the gait and balance measurements performed by use of EMG or IMU outputs, the measurement data is processed in the controller to determine the optimum change in the shape of the shoe, to compensate in real time for the anomalies found in the EMG or IMU measurement data output. The relationship between EMG and gait anomalies has been described in an article entitled "The effect of manipulation of the center of pressure of the foot during gait on the activation patterns of the lower limb musculature" by Y. Goryachev et al, published in Journal of Electromyography and Kinesiology, Vol. 21, pages 333-339 (2011), in which there is described the correlation between the muscle activity of the lower limbs and lower spine, and the GRF and CLP of the subject's foot contact. As described in that article, the coronal shifts of the COP correspond with activation changes of coronal muscles in a way that compensates for the perturbation (i.e., a medial COP shift will cause an increase in the activation of laterally positioned muscles) and that a sagittal COP shift will correspond with activation changes of sagittal muscles, in order to maintain force and torque equilibrium within the lower kinematic chains. Thus, measurement of defective muscle activity can be used to adjust the sole shape iteratively, in order to obtain a predictable correction of the muscle activity, to relieve the gait disorder.

The shoe of the present disclosure, thus allows shifting of the Center of Pressure trajectory autonomously and continuously to an optimum position, to enable an efficient novel treatment method for patients suffering from neuromuscular and orthopedic disorders.

The pressure profile readings, or the EMG readings, or the MU readings, depending on the measured data used, can also be stored off-line and later used for analyzing and diagnosing gait and instability events accruing during locomotion. In addition, a user interface can be provided for controlling the use of the pressure or other parameters. Feedback may be provided via the user interface to the controller, either by the user him/herself, or by an attendant therapist, in order to additionally define the change in the shape of the sole in light of the goal function.

Specific ways in which the change in the shape of the sole of the shoe can be achieved include mechanical change in the physical shape of the sole, such as by moving elements, most conveniently using miniature electric motors within the sole, to change the shape of the sole, or by use of a sole having spatially adjustable stiffness, such that the COP of the user's foot can be amended by changing the softness profile of the sole.

Each of the system components is now summarized. In the force measurement example used in this disclosure to illustrate the system, the insole device may be comprised of upper and lower surfaces, conveniently produced by a 3-D printing process, according to the size and shape of the user's foot, with indentations for circular supports and for pressure sensing devices.

The robotic platform may contain a mechanical system for generating controlled adjustment of the position of the moveable elements, in response to feedback provided to the robotic platform. The movement of the elements may be programmed by the algorithm imbedded in the controller in two or three dimensions. As an alternative to mechanically moveable elements, the mechanical properties of the sole may be modified by generating the sole or elements from materials that harden or soften upon activation, as, for example, by an applied electric current. The changes in the properties of the sole occur in real-time, in response to feedback from the system.

The pressure elements of the insole device and the movable elements of the robotic platform are integrated components of the robotic shoe. Input from the insole device may be provided via a control and energy center to a real-time unit which reads and records the pressure measurements. This information may be provided both to an external memory for clinical analysis, and to the main controller. The main controller may collect the data, calculate gait parameters and constraint parameters, and define the movement of the elements in light of the programmed goal. The calculations may also be made in response to input from the user or an attending therapist via the user interface. The main controller then may provide feedback to the robotic system to modify the element movements, or the stiffness profile of the variable stiffness sole, as programmed by the user or operator.

For systems using measurements other than the insole force measurement, the shoe need not include the force measurement insole, but the controller does require input of the alternative measured data.

There is thus provided in accordance with an exemplary implementation of the devices described in this disclosure, a robotic shoe, comprising:
(i) at least one sensor whose output provides information regarding the gait of a wearer of the shoe;
(ii) a control system adapted to receive output signals from the at least one sensor, and to process the signals in real time to provide a dynamic representation of the wearer's walking pattern, and
(iii) at least one element mounted on the sole of the shoe, providing ground contact for the shoe, the at least one element being controlled to move in the plane of the sole according to output signals received from the control system, such that the forces acting on the wearer's foot and lower limb can be adjusted in real time according to the wearer's walking pattern.

In such a robotic shoe, the at least one sensor may be a plurality of pressure sensors mounted in a composite insole over the area of the sole, the sensors being configured to measure the pressure distribution pattern when the shoe is in contact with the ground. Alternatively, the at least one sensor may be either an electromyography sensor, adapted to be attached to the wearer at a muscle to be monitored, or an inertial measurement unit, adapted to be carried by the wearer of the shoe in a location which enables measurement of the motion in the pelvic or other lower body region of the wearer. In the case of pressure sensors, the pressure distribution pattern may comprise the center of pressure of the foot.

In any of the above described robotic shoes, the at least one element may be controlled to move with at least two degrees of freedom. Additionally, the at least one element may be two physical elements, mounted in fore and aft locations of the sole.

Further implementations of the above described robotic shoe may have an output device displaying the wearer's walking pattern, such that clinically relevant features of the wearer's gait can be determined.

In other implementations, the robotic shoe may further comprise electro-mechanical actuators for moving the elements. Furthermore, one degree of freedom of motion may be provided by fore and aft motion of an element, and another degree of freedom of motion may be provided by rotation of an element around a pivot axis offset from the center of rotation of that element. In the latter case, the shoe may further comprise a pair of linear rails for each of the at least one element, along which each element can move fore and aft, and a worm gear on each side of each element, the worm gears meshing with a geared wheel attached to each element. In such a case, rotation of the worm gears on each side of an element in the same direction, is configured to generate linear motion of their associated element, while rotation of the worm gears on each side of an element in opposite directions is configured to generate rotational motion of its associated element. Finally, in those implementations incorporating pressure sensors, the positions of the pressure sensors may be arranged such as to provide a measure of the foot center of pressure.

According to yet other implementations of the robotic shoe of the present disclosure, the sole may comprise a smart material responsive to external stimuli and the at least one element may be a region of the sole activated by an external stimulus. In such a case, the smart material may be activated by an applied electrical voltage. Additionally, the smart material may be polarized.

Finally, in the above described robotic shoes, at least some of the elements may be convex shaped. Additionally, at least some of the elements may be biomechanical. Furthermore, at least some of the elements may move with three degrees of freedom.

According to yet another implementation disclosed herein, there is provided a method of treating gait disorders in a subject, comprising the steps of:
(a) measuring signals generated by at least one sensor which provides information regarding the subject's ambulation or standing pose;
(b) inputting the measured signal data to a controller, adapted to calculate current gait parameters from the pressure signal data;
(c) using a predetermined algorithm to determine the change in ground reaction forces required in at least one foot of the subject, to improve the gait parameters;
(d) moving at least one element in the robotic shoe, in accordance with the required change in ground reaction forces; and
(e) repeating steps (a) to (d) to providing dynamic real-time feedback to improve the subject's gait.

In such a method, the measuring may be performed using the robotic shoe to measure pressure signals generated by a plurality of sensors in an insole device of the shoe during the subject's ambulation or standing pose. Alternatively, the at least one sensor may be an electromyography sensor, adapted to be attached to the wearer on the skin opposite a muscle to be monitored, or it may be an inertial measurement unit, adapted to be carried by the wearer of the shoe in a location which enables measurement of the motion in the pelvic or other lower body region of the wearer.

In any of these methods, the at least one element may comprise at least one moveable physical protrusion that defines the position of the ground reaction force of the subject's foot. Alternatively, the at least one element may be a region of the sole of the shoe, the sole being constructed of a smart material whose stiffness is controllable by an external stimulus.

BRIEF DESCRIPTION OF THE DRAWINGS

The present invention will be understood and appreciated more fully from the following detailed description, taken in conjunction with the drawings in which.

DETAILED DESCRIPTION

Figure 1:
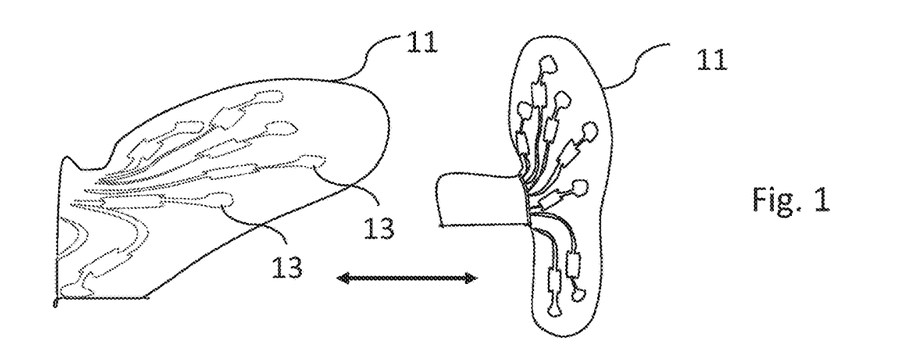
FIG. 1 shows the lower surface of an insole device of a robotic shoe of the type described in the present disclosure.
Figure 2:
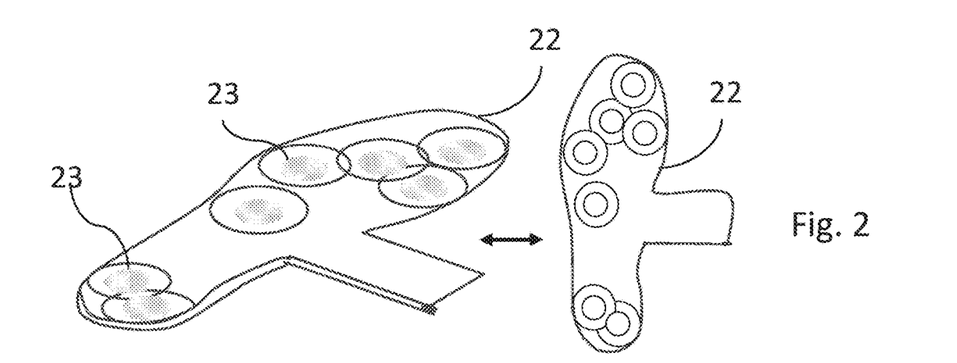
FIG. 2 shows the upper surface of the insole device.

Reference is now made to FIGS. 1 and 2, which illustrate schematically in isotropic and plan views, the lower and upper surfaces of an exemplary insole device of the robotic shoes of the present application, which can be custom designed specifically for the feet of the subject undergoing evaluation. The detailed description section of this disclosure, describes the force sensor implementation, this being the simplest to implement, but it is to be understood that the disclosure also covers any sensory feedback to the robotic shoe which can be used to correct gait disorders. FIG. 1 illustrates the lower part of the insole device 11, and comprises positions for pressure sensors 13 from whose readings, gait parameters such as center of pressure (COP) trajectory cadence and walking speed, can be collected over time. One convenient supplier of such pressure sensors is Tekscan of South Boston, MA, USA. The lower surface contains built-in channels for the wiring, and regions at the end of each channel for locating the pressure sensors in a straight and uniform platform for the during measurements. In the example illustrated, the insole device contains seven sensors to map the gait forces on the foot with sufficient resolution. The number and location of the sensors are based on commonly accepted practice in the profession, as described in the article "A portable insole plantar pressure measurement system" by J. J. Wertsch et al, as published in *J. Rehabil. Res. Dev.*, vol. 29, pp. 13-8, 1992. The stages determine the location of the seven sensors to perform optimal measurements of the COP trajectory. In other embodiments, additional sensors of various sizes and shapes could be incorporated into the insole device. The sensors are connected by leads running in the channels to the output interface of the shoe. The insole may be advantageously and cost-effectively produced by a flexible 3D printing technique.

Reference is now made to FIG. 2, showing the upper part of the sole 22. In the exemplary implementation shown, the upper surface is a mirror image of the lower surface with circular releases in two different diameters and depths aligned opposite each sensor stage in the lower part. Hard plastic discs 23 are inserted into the smaller releases; combined with the large releases, they together provide a larger sensing area than the sensors themselves would provide. The remaining areas of the upper sole are thicker than the areas of the discs housing wells such that they provide structural support. This structure is only one way in which the sensors may be incorporated into the soles, and it is to be understood that in other implementations, a different structure could be utilized.

Figure 3:
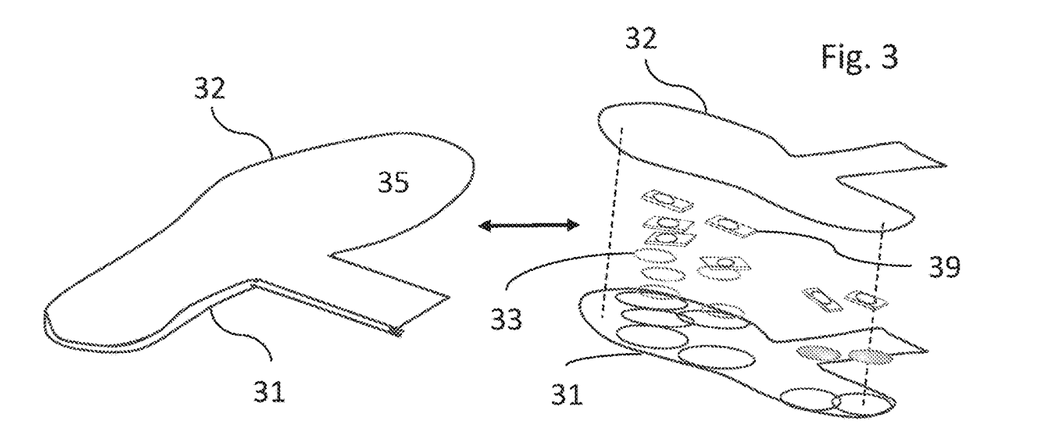
FIG. 3 shows the assembly of the insole device components.

In FIG. 3, shows the assembly of the upper 32 and lower 31 surfaces of the insole device are shown aligned with each other and with the approximate locations of the sensors 39 and discs 33. The components are assembled as shown in the Fig. to create the complete insole device 35. In other implementations, different arrangements of the discs, sensors, and surfaces could be combined.

Figure 4:
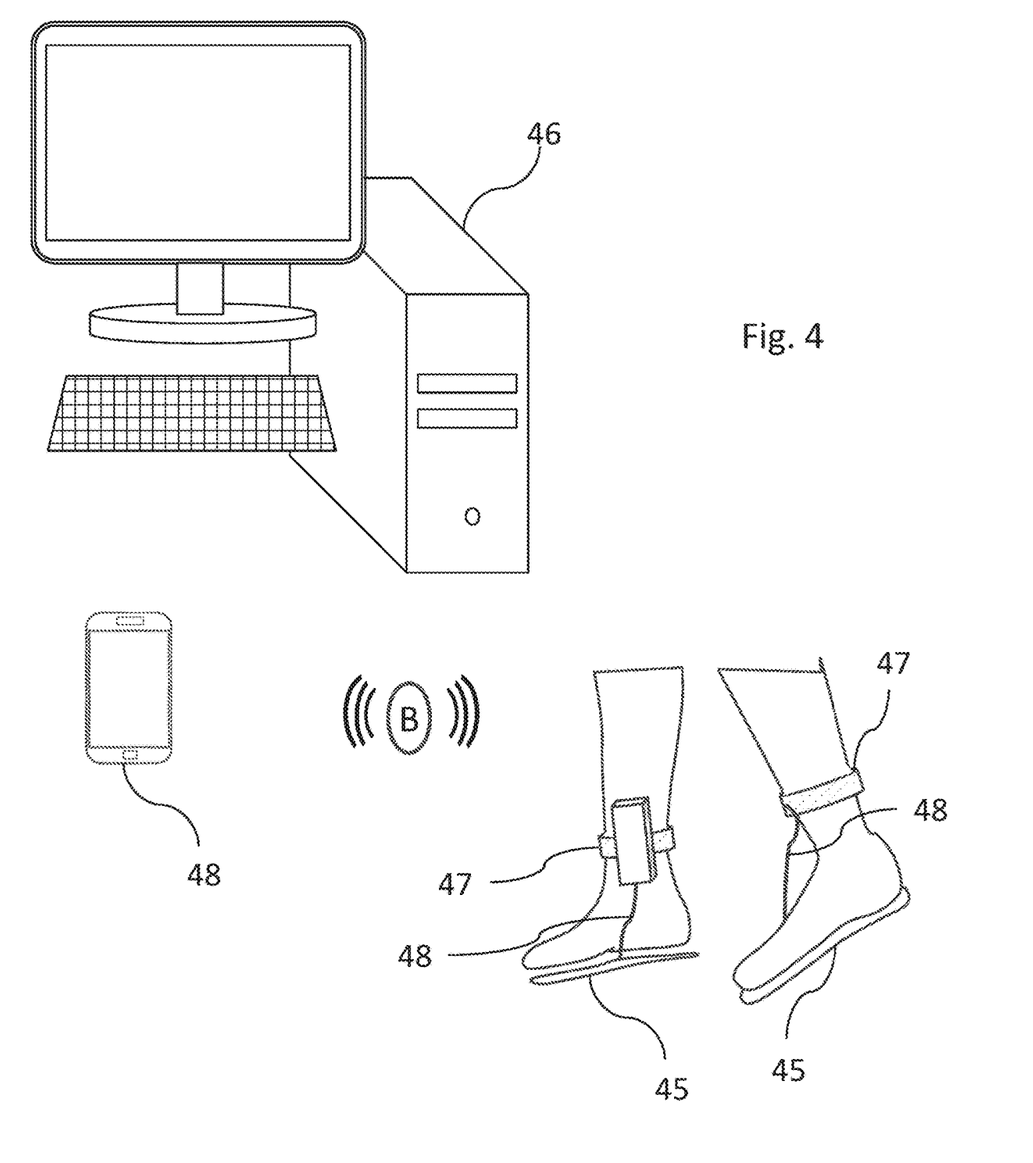
FIG. 4 illustrates schematically a system of the type described in this disclosure, showing the insole of the type described in FIGS. 1 to 3, as would be fitted into a robotic shoe.

Reference is now made to FIG. 4, which illustrates schematically an exemplary system of the type described in this disclosure, showing the insole 45 of robotic shoe, of the type described in FIGS. 1 to 3, cable connected 48 to a local controller 47, which can conveniently be attached to the user's ankle. Alternatively, the local controller can be mounted on or within the shoe itself if miniaturized sufficiently. Data collected from the insole sensors is transferred to the local controller 47 by this wired communication. The local controller 47 may provide the energy sources for the insole assembly 45 of the full robotic shoe (not shown in FIG. 4), and local control of the signals input to and output from the shoe. The sole sensor system is used to continuously monitor the COP, providing a closed controlled loop signal to a robotic platform with movable elements (not shown in FIG. 4). The controller 47 can calculate gait parameters in real time. All data collected by the sensors may also be broadcast in real time to the external control system 46 for use in the patient therapy procedure by the user or by a therapist. The external controller may be a dedicated unit, or a computer 46, or a smartphone 48.

Figure 5A:
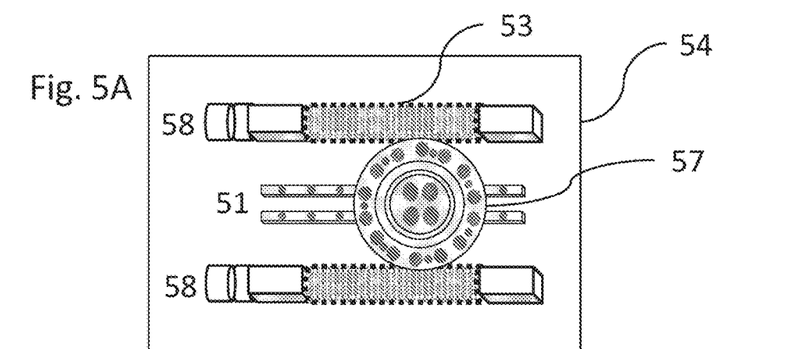
FIGS. 5A to 5C illustrate various views of an exemplary design of the robotic shoe mechanism, using mechanically moved protruding elements located on the sole of the shoe.
Figure 5B:
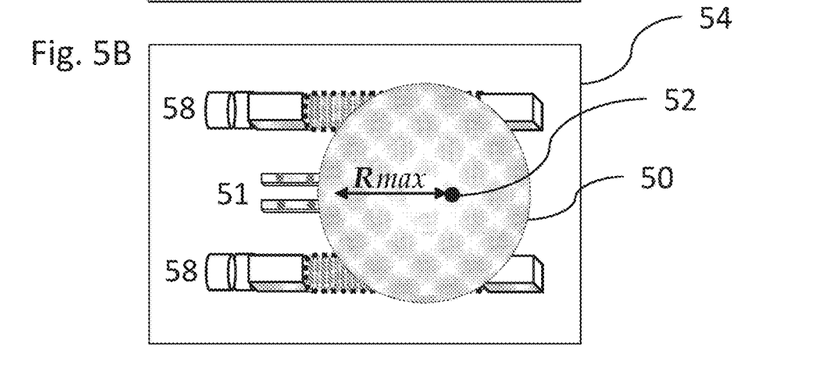
Figure 5C:
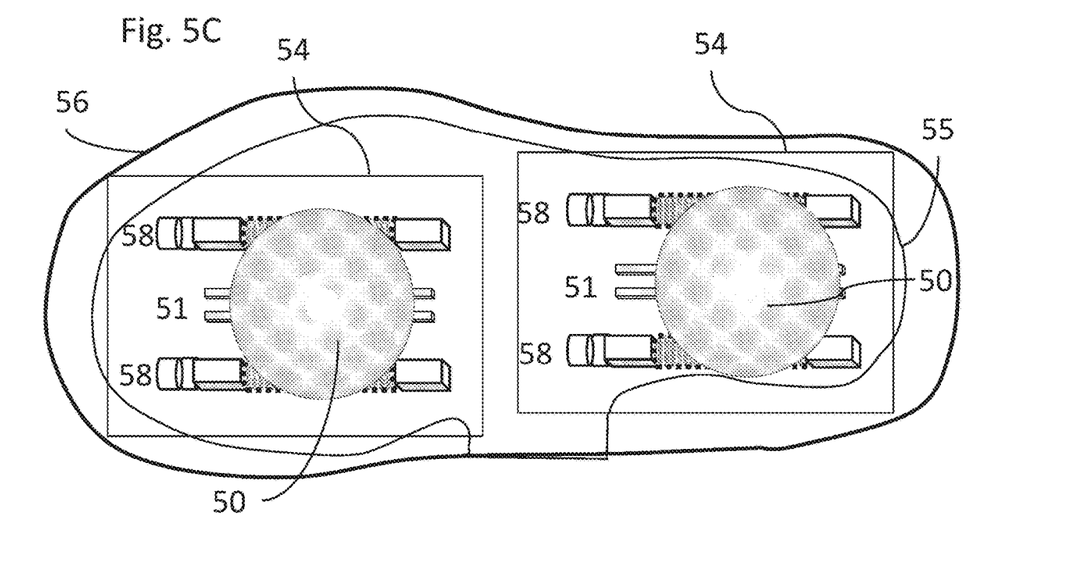

Reference is now made to FIGS. 5A to 5C, which illustrate one exemplary design of the robotic shoe mechanism, using mechanically moved protruding elements 50 located on the sole of the shoe. The robotic platform consists of at least one such adjustable motion generating stages 54, inducing motion into the support elements 50, and attached to a shoe-like base 56. Although there are clinical conditions where motion of the GRF using a single protrusion, is sufficient to assist in solving the subject's problems, most gait problems are better solved using at least two such protrusions. These elements may be convex-shaped, and their movement may be adjusted by mechanical, biomechanical or other means. Furthermore, the elements may be expanded to cover the entire sole, though typically, only two such elements are used, one in the forward area and the other in the rear area of the shoe form. As an alternative to mechanically moveable elements, the robotic platform may be comprised of a material, including smart materials, that respond directly to pressure or to other external stimuli, as will be further described in FIG. 9C hereinbelow.

Each element position can be adjusted individually with two degrees of freedom, by moving along a linear set of rails 51 and around an eccentric axis 52. These two movements allow each element to change its position continuously in the transverse plane of the foot to reach any location in a radius of 100 mm in the example shown, essentially shifting the COP in the desired direction. Each element can move while the wearer is walking, using two independent DC motors 58 actuated during the swing phase of the wearer's steps. For user safety, the device should be mechanically self-locked, which means that the elements should not move as a response to the operated forces and moments during gait, but only as a result of controller commands to the motors 58. In this illustration, $R_{max}$ is the distance between the force location on the biomechanical element—generally the point of contact with the ground—and the shaft, which is the rotation axis of the element.

To obtain two degrees of freedom, as well as mechanical self-locking for each element, each motion generating stage comprises at least two worm-screws 53 connected on both sides of a gear wheel 57. The screws and the wheel are designed to support the forces and moments that would develop on the elements during gait. The element motion mechanism is designed to have linear movement of the wheel riding on two miniature Nippon rails 51. Both worm gears 53 may rotate in the same or opposite directions. When the worm gears rotate in the same direction, the gear wheel 57 and its mounted element 50 undertake linear motion down the rails, the motion direction being dependent on the direction of rotation of the worm gears. When the worm gears rotate in opposite directions, the gear wheel 57 in mesh with the worm screws 53, will rotate around the axis 52, and since the elements are mounted offset to the axis 52 (by a distance $R_{max}$), rotation of the gear wheel 57 will result in an arc-like motion of the protruding element 50, thereby enabling motion in a direction perpendicular to the rails. Rotation of the two worm screws 53 at different speeds will result in linear and rotational motions, thus providing a two dimensional motion trajectory for the element 50. Sliding bearings made of Teflon facilitate all of the motions. In FIG. 5C, two robotic motion platforms 54 are placed in relationship to the insole device 55, showing the relative spatial relationship among them. A single platform or multiple platforms may be used according to the individual subject's requirements.

Figure 6:
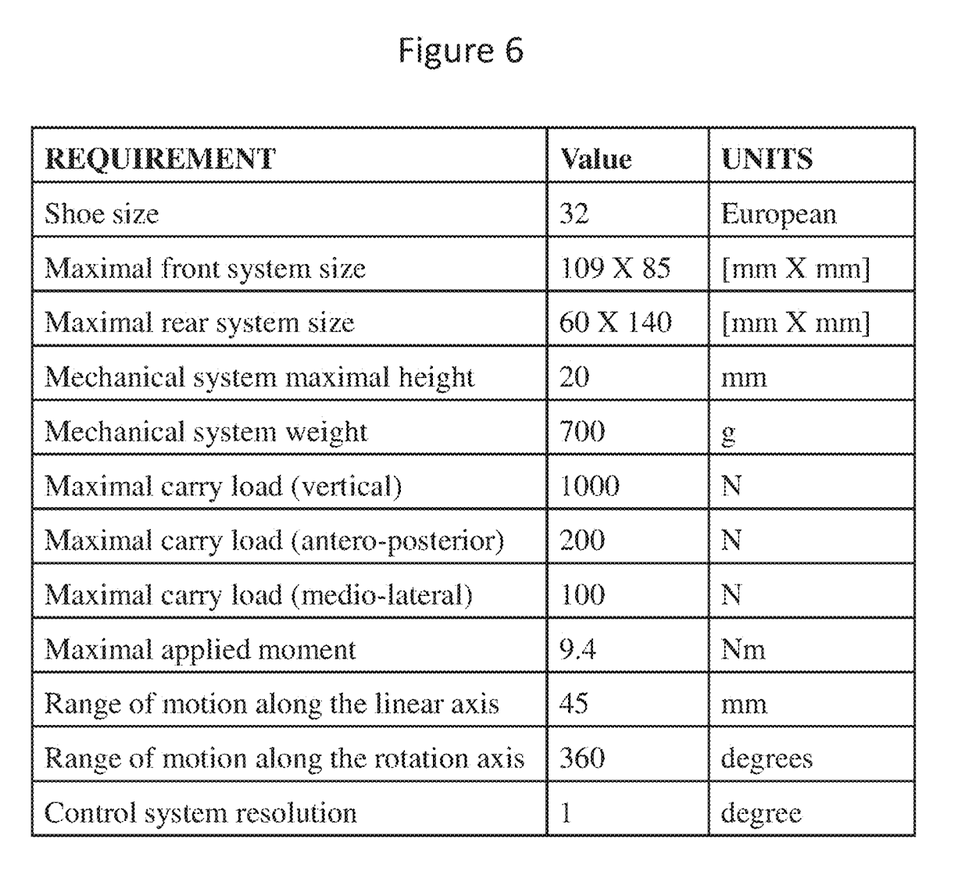
FIG. 6 is a table of required mechanical parameters for a robotic shoe of the type shown in FIG. 5C, designed to support a person weighing 70-80 kg.

Since the device should behave as a shoe-like product, all the mechanical parts and electronics should be located within the spatial limits of the sole, leading to difficult constraints of weight and volume for the robotic platform components and design. An exemplary list of robotic shoe mechanical requirements is provided in FIG. 6, in which the system was designed to support a person weighing 70-80 kg, translating into approximately 1000 N for the vertical force and up to 200 N for the shear forces on the system. The maximum developed moment on the system shaft in such conditions is 9.4 Nm. Shear stresses on the worm screw should be smaller than the shear stresses allowed by the material and the geometric properties of the screw. In the example described, each of the Nippon rails can handle a three of up to 580 N, so together they can bear more than 1000 N. Thus, the system in this exemplary illustration is capable of bearing the forces generated by the subject wearing the robotic shoe. Other exemplary cases may use components manufactured of different materials to lighten the weight of the device.

The robotic shoe contains a local and simplified location controller, which, in one typical implementation, uses a magnetic encoder with six magnetized pole pairs and two sensors, giving together a resolution of 12 pulses per one motor cycle. An enhanced control system using the insole device for closed controlled loop on the COP, can provide monitoring and control of the COP. However, other types of encoders may also be used.

Figure 7:
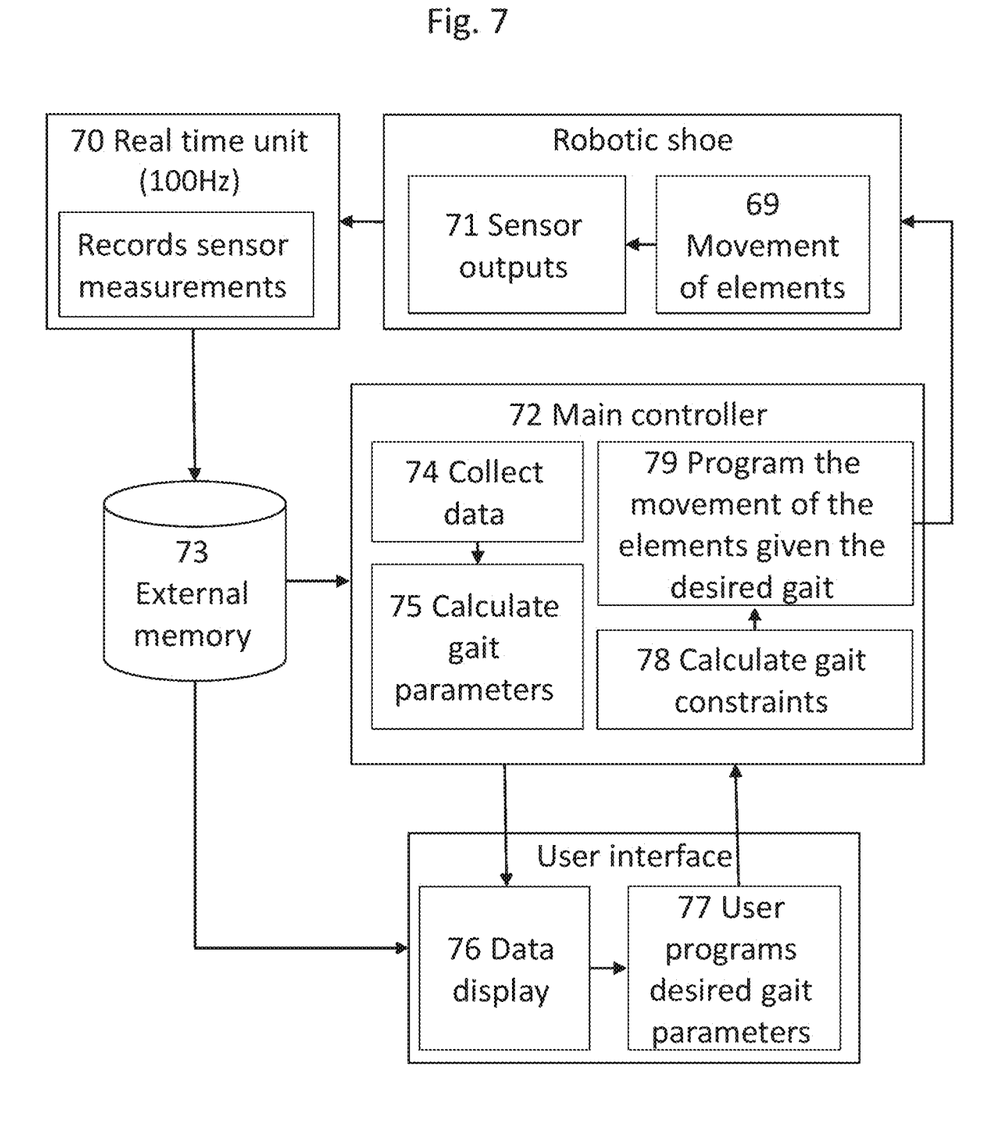
FIG. 7 schematically diagrams the entire system components and their integration and interconnection.

Reference is now made to FIG. 7, which is a block diagram of one exemplary implementation of a complete system, showing the control mechanisms and its operation. The real time unit 70 of the control system receives in real time, sensor measurements used to define gait abnormalities either from the pressure sensors 71 of the robotic shoe, or from other sensors, such as EMG or IMU sensors, and sends the data to either or both the main controller 72 and an external memory 73 for future analysis. The main controller 72 collects the data 74, calculates 75 the COP trajectory and other gait parameters, calculates the gait constraints 77, optionally depending also on inputs 77 from the therapist and/or the user, and generates signals 79 for the motion mechanisms in the shoe, in order to shift the COP as per the seeking function and the constraints defined by the user. The desired COP trajectory can be obtained and controlled to allow various treatment applications such as setting a specific location of the COP trajectory provided by a therapist/physician, implementing a long term treatment protocol, and preserving an optimal COP with variation of the subject's conditions. These decisions can be facilitated by initially viewing the data on a monitor screen 76 in the user interface unit.

Figure 8:
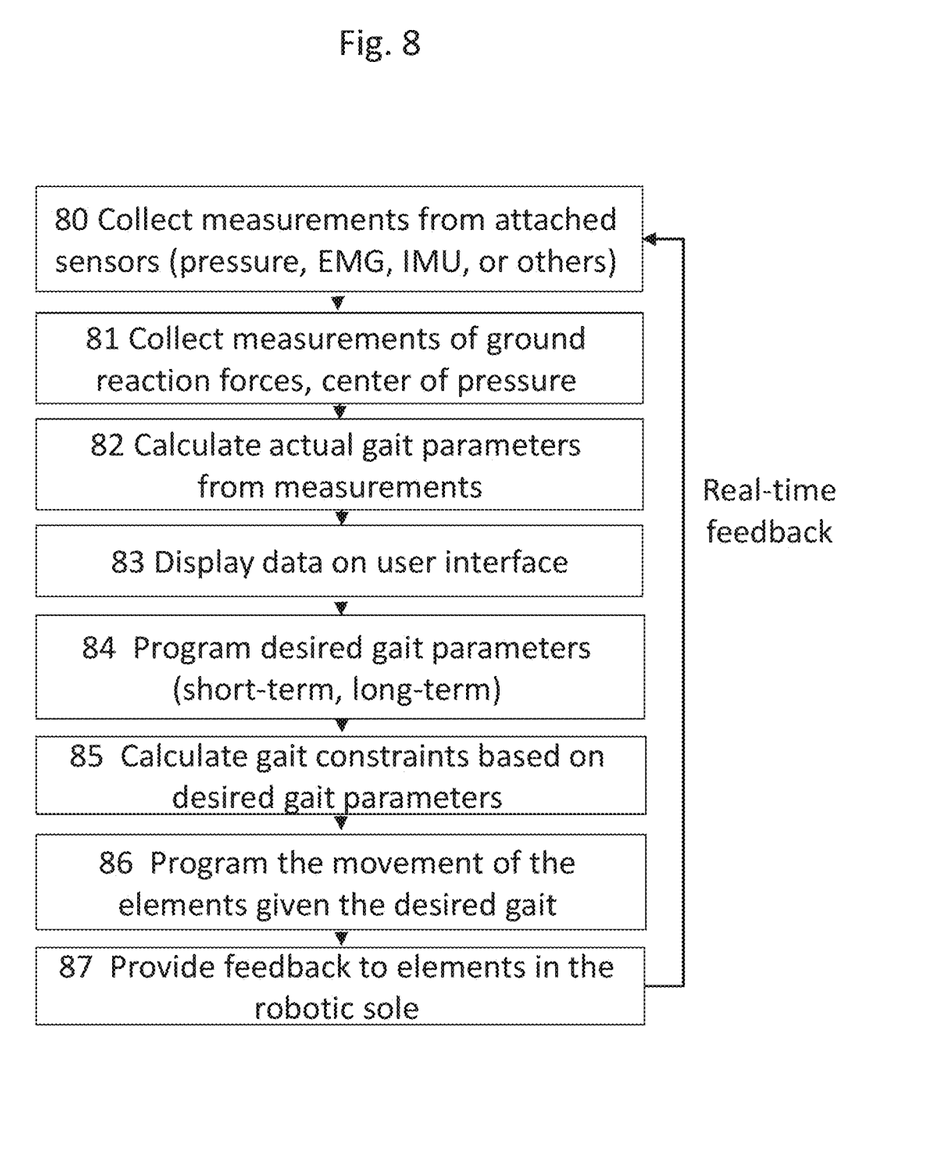
FIG. 8 is an exemplary flowchart describing the steps involved in sensing, calculating, and programming the device.

Reference is now made to FIG. 8, which is an example of a flow chart which could be used to illustrate a possible implementation of the flow of information through the system. In step 80, measurements are made of the signals generated by the sensors used to detect gait problems, during a subject's ambulation or standing pose, whether pressure sensors in the insole device, or EMG measurements performed by sensors attached to the skin of the subject opposite the muscles being monitored, or by an IMU carried by the subject. Measurements of the ground reaction forces (GRP) and COP are collected and transferred in step 81 remotely to the central controller, where current gait parameters are calculated from the measurements in step 82. These data may be displayed in step 83 for the user, either the subject him/herself or the clinical practitioner, who programs desired gait parameters in step 84, according to the clinical outcome desired. These parameters may be for either short-term or long-term usage. Short-term use may be needed to provide feedback to improve or stabilize the gait of a patient with chronic debilitating neuromuscular or orthopedic disease. Long-term use could be used to establish a gait training program as in a rehabilitation setting, for patients after a surgical operation, post-trauma, or in another recovery scenario. Once the selected gait parameters have been programmed into the system, specific gait constraints are calculated in step 85, based on the previously determined desired parameters. In step 86, the required movement of the elements in the robotic platform is programmed in the form of the required motion instructions to the robotic shoe platforms, and is then sent back in step 87 to the elements in the robotic sole, providing dynamic control of the subject's gait. This continuous closed loop system continues to measure COP and GRF, thus providing feedback in real-time to improve the subject's gait.

Figure 9A:
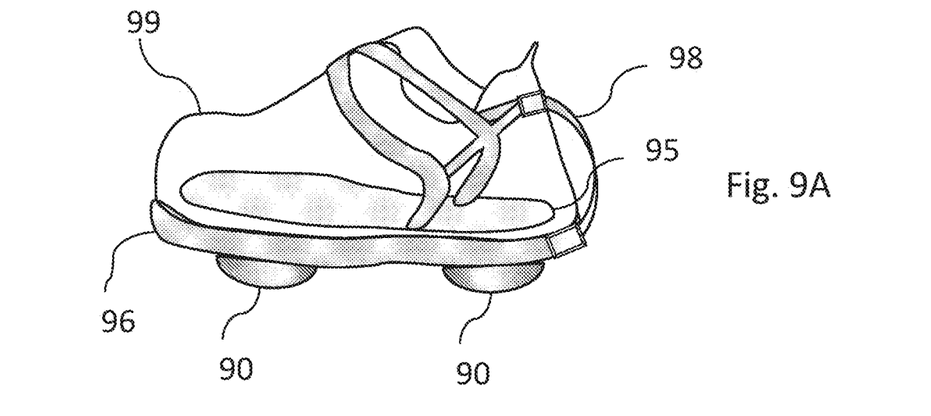
FIGS. 9A to 9C illustrate different isometric views of exemplary robotic shoes, and the various components including the insole device and robotic platform with movable elements or hardness regions.
Figure 9B:
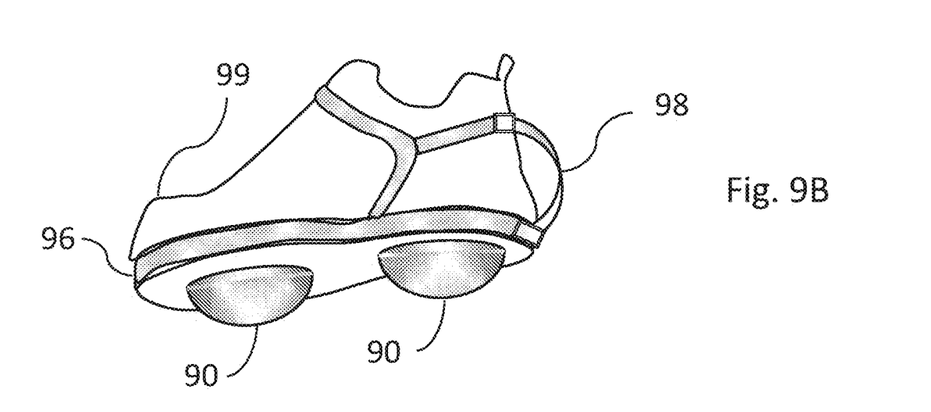
Figure 9C:
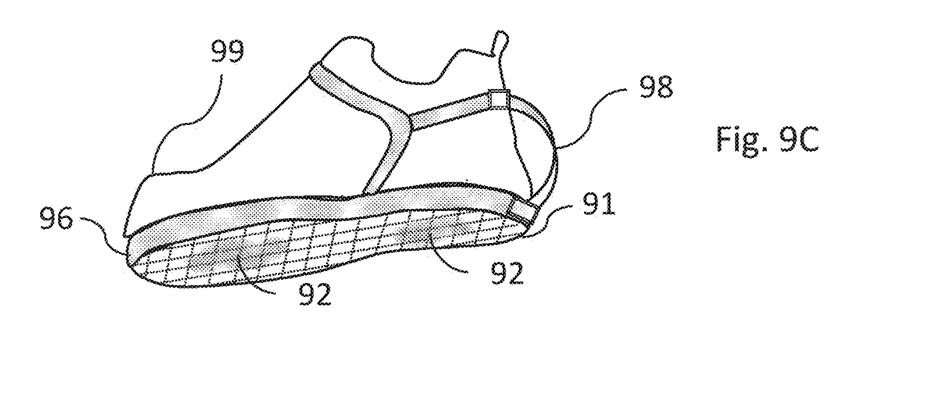

Reference is now made to FIGS. 9A to 9C, which show isometric views of versions of the robotic shoe of the present disclosure, from a side view in FIG. 9A, and a bottom view in FIGS. 9B and 9C. FIGS. 9A and 9B illustrate mechanically driven elements 90, as described in FIG. 5C. The insole device 95 is shown in combination with the robotic platform 96 as they fit together in the form of a shoe 99 to be worn by the subject undergoing evaluation and treatment. The movable elements 90 supply the contact surface with the ground. The upper area of the shoe contains the local energy and control device (not shown) which both feeds information, such as pressure measurements, to the remote or the local controller (not shown) and receives programmed signals from the remote or local controller, which it then transfers to the robotic platform 96 via wires 98.

FIG. 9C illustrates a further method of moving the COP of the subject during motion, as an alternative to mechanically moveable elements. In this implementation, the sole of the shoe 91 is comprised of a material whose stiffness can be varied by application of an activating effect, such that different regions of the sole harden or soften upon activation, as, for example, by use of an applied electric current, which can be applied by means of an embedded grid of wires 91 within the sole, selected by use of a gated array network, as is known in the semiconductor arts. The controller, in response to the measured pressure map of the user's gait, generates a pattern of activated regions in a spatially-determined manner, such that the desired specific areas of the sole 92 harden or soften, according to the program determined by the therapist or the subject. Use of this method and materials enables the generation of what are effectively protruding and less protruding areas of the sole, by adjusting the hardness of the sole material accordingly, yet without any significant mechanical or physical movement of the protruding areas. In the regions where the stiffness is increased, the subject feels the major effect of the ground reaction force; in those regions where the stiffness of the sole is not increased, the material just relaxes under the pressure of the subject's foot, leaving the harder regions to provide the main reactive force. Thus, without the need to generate any physical motion, the points of major ground contact pressure can be moved around in response to the requirements which the controller generates to move the COP of the subject. Thus, for instance, if the pressure measurement information indicates the need to shift the COP and GRF in a certain direction, that can be achieved by softening the sole in the direction in which it is desired to achieve the shift. The increased softness will cause the subject's foot pressure to move in that direction. Alternatively, the sole can be hardened in the direction away from which it is desired to shift the COP and GRF. Such shifts can be generated in any direction within the two-dimensional plane of the sole. It should thus be emphasized that using this implementation, there may be clinical situations in which the therapeutic effect may be achieved by having only a single hardened area, which is thus equivalent to only a single virtual protruding area, as previously suggested. In addition, such a variable hardness sole does not have to be constrained to the well-known concept of having a single protrusion in the forward region of the sole, and one in the aft region, since the hardened sole of this implementation can be programmed to attain any shape of hardness, and not just discrete virtual protrusions. Thus, it is possible to harden different lateral portions of the sole, besides different longitudinal portions.

Since the hardness level can also be selected by the level of the activating electric current—for those materials using electrical activation—it is possible to select also the height of the correction by the virtual protrusion, thereby providing correction capability also in the third dimension, and not only across the two dimensions in the plane of the shoe sole. This may enable further possibilities for correction of the subject's gait characteristics. In order to provide real-time height adjustment in the mechanical implementation of FIG. 5C, and FIGS. 9A and 9B, a controlled z-axis drive mechanism must be incorporated into the robotic shoe platform.

A number of different types of smart materials can be used for implementing the system described in FIG. 9C. Numerous such materials exist, and although some of them are based on heating effects, which currently may be too slow for use in the present application, smart materials are being developed based on phase transitions in molecules, such as bismuth iron oxide molecules. These materials have very fast and substantial changes in their stiffness, making them suitable for use in the robotic shoes of the present disclosure. Furthermore, electrorheological (ER) or magnetorheological (MR) fluids are available which provide, with the application of an applied electric or magnetic field respectively, rapid changes in viscosity, with a response time of a few milliseconds. Such an application is described in US Published Patent Application 2016/0235160, to Y. N. E. Lam et al, for "Flexible Cushioning Device for Shoes and Methods of Producing the Same". In this application, there is described an adjustable flexible cushioning device for building into high-heeled shoes, in order to provide a custom-made cushioning device for the user's shoe. The profile of this cushioning insole is based on a static premeasure of the pressure distribution of the plantar surface of the user's foot, based on a Pedar pressure measuring system. No suggestion of any real time dynamic feedback is made in this application.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A robotic shoe system, comprising:
at least one sensor whose output provides information regarding the gait of a wearer of the shoe;
a control system adapted to receive output signals from the at least one sensor, and to process the signals in real time to provide a dynamic representation of the wearer's walking pattern; and
at least one element mounted on a sole of a shoe, providing ground contact for the shoe,
wherein the at least one element is configured to be controlled to move in the plane of the sole, according to output signals received from the control system, such that forces acting on the wearer's foot and lower limb can be adjusted in real time according to the wearer's walking pattern;
wherein the at least one element is configured such that at least one degree of freedom of motion is provided by fore and aft motion of the at least one element, and another degree of freedom of motion is provided by rotation of an element around a pivot axis offset from a center of rotation of that element; and
further comprising a pair of linear rails for each of the at least one element, along which each element can move fore and aft, and a worm gear on each side of each element, the worm gears meshing with a geared wheel attached to each element.

2. The robotic shoe system according to claim 1, wherein the at least one element is configured to be in contact with the ground to provide ground contact for the shoe, the at least one element being controlled to move horizontally relative to the ground and within the shoe, within a horizontal two-dimensional plane of the sole defining the plane of the sole, according to output signals received from the control system, such that a point of ground contact of a ground reaction force exerted by the ground directly on the at least one element in contact with the ground is shifted horizontally relative to the sole of the shoe, causing the forces acting on the wearer's foot and lower limb to be adjusted in real time according to the wearer's walking pattern, by horizontal movement, relative to the sole of the shoe, of the ground contact provided by the at least one element, by horizontal movement of the at least one element in the at least one element's entirety.

3. The robotic shoe system according to claim 1, wherein the at least one sensor is a plurality of pressure sensors mounted in a composite insole over the area of the sole, the sensors being configured to measure a pressure distribution when the shoe is in contact with the ground.

4. The robotic shoe system according to claim 3, wherein the pressure distribution pattern comprises a center of pressure of the foot.

5. The robotic shoe system according to claim 1, wherein the at least one sensor is an inertial measurement unit, adapted to be carried by the wearer of the shoe in a location which enables measurement of motion in a pelvic or other lower body region of the wearer.

6. The A robotic shoe system according to claim 1, wherein the at least one element is two physical elements, mounted in fore and aft locations of the sole.

7. The robotic shoe system according to claim 1, further comprising an output device displaying the wearer's walking pattern, such that clinically relevant features of the wearer's gait can be determined.

8. The robotic show system according to claim 1, further comprising electro-mechanical actuators for moving the at least one element.

9. The robotic show system according to claim 1 wherein rotation of the worm gears on each side of each element in the same direction, is configured to generate linear motion of the element associated with the worm gears, while rotation of the worm gears on each side of each element in opposite directions is configured to generate rotational motion of the element associated with the worm gears.

10. The robotic show system according to claim 1 in which at least one of the at least one element is convex shaped.

11. The robotic show system according to claim 1 in which at least one of the at least one element is biomechanical.

12. A method of treating gait disorders in a subject, comprising the steps of:
(a) providing a robotic shoe system according to claim 11;
(b) measuring signals generated by the at least one sensor which provides information regarding the subject's ambulation or standing pose;

(c) inputting measured signal data to the control system, wherein the control system is adapted to calculate current gait parameters from pressure signal data;

(d) using a predetermined algorithm to determine a change in a ground reaction force required in at least one foot of the subject, to improve the gait parameters;

(e) moving the at least one element within the robotic shoe horizontally relative to the ground and within the shoe, within a horizontal two-dimensional plane of the sole of the shoe defining the plane of the sole, the at least one element being in contact with the ground to provide ground contact for the shoe, to cause horizontal movement, relative to the sole of the shoe, of ground contact provided by the at least one element, by horizontal movement of the at least one element in the at least one element's entirety, in accordance with a required change in the ground reaction force, such that a point of ground contact of the ground reaction force exerted by the ground directly on the at least one element in contact with the ground is shifted horizontally relative to the sole of the shoe, causing forces acting on the subject's foot and lower limb to be adjusted in real time according to the subject's walking pattern; and (f) repeating steps (b) to (e) to provide dynamic real-time feedback to improve the subject's gait.

13. The method according to claim 12, wherein the measuring is performed using the robotic shoe to measure pressure signals generated by a plurality of sensors in an insole device of the shoe during the subject's ambulation or standing pose.

14. The method according to claim 12, wherein the at least one sensor is an inertial measurement unit, adapted to be carried by the wearer of the shoe in a location which enables measurement of motion in a pelvic or other lower body region of a wearer.

15. The method according to claim 12, wherein the at least one element comprises at least one moveable physical protrusion that defines the position of the ground reaction force of the subject's foot.

* * * * *